United States Patent [19]

Engelhardt et al.

[11] Patent Number: 4,931,497
[45] Date of Patent: Jun. 5, 1990

[54] HYDROPHILIC SWELLABLE GRAFT POLYMERS FROM MALEIC ANHYDRIDE-ALKYLENE SUBSTRATE

[75] Inventors: Friedrich Engelhardt; Ullrich Riegel, both of Frankfurt, Fed. Rep. of Germany

[73] Assignee: Cassella Aktiengesellschaft, Frankfurt am Main, Fed. Rep. of Germany

[21] Appl. No.: 264,022

[22] Filed: Oct. 28, 1988

[30] Foreign Application Priority Data

Nov. 13, 1987 [DE] Fed. Rep. of Germany ....... 3738602

[51] Int. Cl.$^5$ .............................................. C08L 67/06
[52] U.S. Cl. ........................................ 525/42; 525/48; 604/358
[58] Field of Search .............................. 525/42, 48, 43; 526/240, 278, 287

[56] References Cited

U.S. PATENT DOCUMENTS

| | | | |
|---|---|---|---|
| 2,957,843 | 10/1960 | Anderson | 525/42 |
| 3,990,459 | 11/1976 | Papantoniou | 525/327.4 |
| 4,100,127 | 7/1978 | Fukusaki | 525/42 |
| 4,275,176 | 6/1981 | Login | 525/48 |

*Primary Examiner*—Christopher Henderson
*Attorney, Agent, or Firm*—Connolly and Hutz

[57] ABSTRACT

The present invention relates to hydrophilic swellable graft polymers which consist, in random distribution, to the extent of 0.5 to 20% by weight of radicals of the general formula I

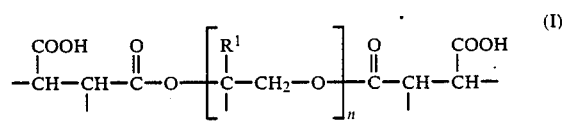

79 to 99% by weight of radicals containing an acid group, of the general formula II

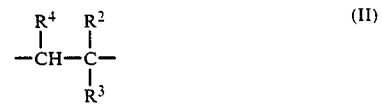

and 0.1 to 2% by weight of crosslinking structures originating from monomers with at least two olefinically unsaturated double bonds, wherein the radicals $R^1$ to $R^4$ and n have the meanings given in claim 1, these graft polymers being used as absorbants for water and aqueous solutions.

6 Claims, No Drawings

HYDROPHILIC SWELLABLE GRAFT POLYMERS FROM MALEIC ANHYDRIDE-ALKYLENE SUBSTRATE

The present invention relates to hydrophilic swellable graft polymers which consist, in random distribution, to the extent of 0.5 to 20% by weight of radicals of the general formula I

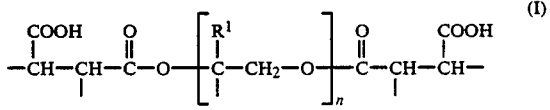

to the extent of 79 to 99% by weight of radicals containing an acid group, of the general formula II

and to the extent of 0.1 to 2% by weight of radicals of a crosslinking agent which originate from monomers with at least two olefinically unsaturated double bonds, wherein n denotes 2 to 300,
$R^1$ denotes hydrogen or methyl.
$R^2$ denotes hydrogen, methyl or ethyl,
$R^3$ denotes the carboxyl group, the sulphonyl group, the phosphonyl group, which can optionally be esterified with alkanol with 1 to 4 carbon atoms, or a group of the formula

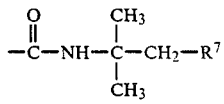

wherein $R^7$ stands for the sulphonyl group or the phosphonyl group, and $R^4$ denotes hydrogen, methyl, ethyl or the carboxyl group, and their preparation and use as absorbants for water and aqueous solutions, for example in hygiene articles, for soil improvement or as filtration auxiliaries.

Swellable polymers which absorb aqueous solutions are used for the production of tampons, nappies, sanitary towels and other hygiene articles and as water retention agents in agricultural horticulture.

Known absorption resins of this type include crosslinked carboxymethylcellulose, partly crosslinked polyalkylene oxide, hydrolysis products of starch/acrylonitrile graft copolymers and partly crosslinked polyacrylic acid salts.

These known polymers all exhibit disadvantages, especially in the absorption of aqueous electrolyte solution and of blood and urine.

According to the current prior art, when the absorption capacity is high the gel strengths achieved in the swollen polymer particles are too low. Tacky compositions form, which impair the absorbency of the products produced with these polymers.

It is known that the gel strength and the rate of liquid uptake can be increased by increasing the crosslinking density, but at the same time the absorption capacity is thereby reduced. This procedure is undesirable inasmuch as the absorption capacity is the most important property of the polymer.

The object of the present invention is to provide modified polymers which absorb aqueous solutions, have a high degree of absorption and at the same time do not form tacky hydrogel particles of high gel strength in the swollen state.

Surprisingly, it has now been found that the desired pattern of properties is achieved by the graft polymers according to the invention, since their macromolecular network has the physical effect of an increase in the gel strength or gelling power of the swollen polymer and an improved electrolyte tolerance.

Preferred products according to the invention consist to the extent of 0.5 to 15% by weight of radicals of the general formula I, 84 to 99% by weight of radicals of the general formula II and 0.1 to 1.8% by weight of crosslinking structures originating from monomers with at least two olefinically unsaturated double bonds.

Particularly preferred products according to the invention consist to the extent of 1 to 10.5% by weight of radicals of the general formula I, 88 to 98.5% by weight of radicals of the general formula II and 0.3 to 1.5% by weight of crosslinking structures originating from monomers with at least two olefinically unsaturated double bonds.

In the graft copolymers according to the invention, the radicals of the general formula I can all have exactly the same structure, but they can also differ from one another in respect of the radical $R^1$ and/or the number n. Thus, in respect of $R^1$, hydrogen ano methyl can alternate randomly, but it is also possible for larger polymer sections in which $R^1$ denotes in each case only hydrogen or only methyl to follow one another.

In the radicals of the general formula II, $R^2$ preferably denotes hydrogen or methyl. $R^3$ preferably stands for the carboxyl group, the sulphonyl group or the phosphonyl group. The carboxyl group is particularly preferred. $R^4$ preferably denotes hydrogen.

The crosslinking structures mentioned can be derived from all suitable monomers with at least two olefinically unsaturated double bonds.

Examples of suitable monomers are compounds which contain at least two alkenyl groups, for example vinyl or allyl, or at least two alkenoyl groups, for example acrylate or methacrylate.

The crosslinking structures are preferably derived from monomers containing 2, 3 or 4 ethylenically unsaturated double bonds.

The crosslinking structures are particularly preferably derived from bisacrylamidoacetic acid, trimethylolpropane triacrylate or tetraallyloxyethane.

Especially preferred graft polymers according to the invention are those which contain several of the above-mentioned preferred or particularly preferred features.

The graft polymers according to the invention can be prepared by known polymerization processes. Polymerization in aqueous solution by the so-called gel polymerization process is preferred. In this, 15-50% strength aqueous solutions of the comonomers are polymerized with known suitable catalyst systems without mechanical mixing by utilizing the Trommsdorff-Norrish effect (Bios Final Rep. 363.22; Makromol. Chem. 1, 169 (1947)).

The polymerization reaction can be carried out in the temperature range between 0° C. and 130° C., preferably between 10° C. and 100° C., either under normal pressure or under increased pressure. As is customary, the polymerization can also be carried out under an inert gas atmosphere, preferably under nitrogen.

The polymerization can be initiated by high-energy electromagnetic radiation or the customary chemical polymerization initiators, for example organic peroxides, such as benzoyl peroxide, tert.-butyl hydroperoxide, methyl ethyl ketone peroxide and cumene hydroperoxide, azo compounds, such as azodiisobutyronitrile, and inorganic peroxy compounds, such as $(NH_4)_2S_2O_8$, $K_2S_2O_8$ or $H_2O_2$, if appropriate in combination with reducing agents, such as sodium bisulphite, and iron(II) sulphate, or redox systems which contain as the reducing component an aliphatic or aromatic sulphinic acid, such as benzenesulphinic acid and toluenesulphinic acid or derivatives of these acids, such as, for example, Mannich adducts of sulphinic acid, aldehydes and amino compounds, such as are described in German Patent Specification No. 1,301,566. As a rule 0.03 to 2 g of the polymerization initiator are employed per 100 g of total monomers.

The quality properties of the polymers can be improved further by after-heating the polymer gels in the temperature range from 50 to 130° C., preferably 70 to 100° C., for several hours.

The copolymers according to the invention which are prepared in this way and are in the form of aqueous jellies can be obtained in the solid form by mechanical comminution by known drying processes using suitable apparatuses and can be put to use.

Graft polymers according to the invention are thus expediently obtained when 0.5 to 20% by weight, preferably 0.5 to 15 and in particular 1 to 10.5% by weight, of a polyalkylene oxide compound of the general formula Ia

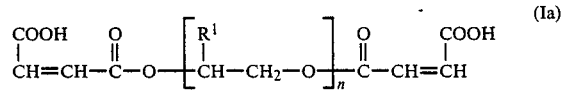

or an alkali metal salt, ammonium salt or amine salt thereof, 79 to 99% by weight, preferably 84 to 99 and in particular 88 to 98.5% by weight, of an unsaturated acid of the general formula IIa

or an alkali metal salt, ammonium salt or amine salt thereof, and 0.1 to 2% by weight, preferably 0.1 to 1.8 and in particular 0.3 to 1.5% by weight, of a monomer with at least two olefinically unsaturated double bonds, wherein the radicals $R^1$ to $R^4$ and the number n the abovementioned meanings, are reacted under the conditions of gel polymerization.

The polyalkylene oxide compounds of the general formula Ia can be obtained by a simple esterification reaction between maleic anhydride and polyalkylene oxides. Examples of suitable polyalkylene oxides are polyethylene glycol, polypropylene glycol, block copolymers of polyethylene oxide and polypropylene oxide blocks and random ethylene/propylene oxide copolymers.

The monomers of the formula IIa are known compounds, such as, for example, acrylic acid, methacrylic acid, vinylsulphonic acid, maleic acid, fumaric acid, crotonic acid, 2-acrylamido-2-methylpropanesulphonic acid, 2-acrylamido-2-methylpropanephosphonic acid and vinylphosphonic acid and half-esters thereof.

The polyolefinic monomers used as crosslinking agents are customary products. Examples are bisacrylamidoacetic acid, trimethylolpropane triacetate and tetraallyloxyethane.

The graft polymers according to the invention are outstandingly suitable as absorbants for water and aqueous solutions, so that they can advantageously be used as water retention agents in agricultural horticulture, as filtration auxiliaries and in particular as absorbant components in hygiene articles, such as nappies, tampons or sanitary towels.

The following Examples 1 to 13 illustrate the preparation of graft polymers according to the invention.

EXAMPLE 1

5,169 g of demineralized water are taken in a polyethylene bucket which has a capacity of 10 l and is well-insulated by a foamed material of plastic, 1,000 g of sodium bicarbonate are dispersed therein and 1,888 g of acrylic acid are slowly metered in so that the reaction solution is prevented from foaming over, this being cooled to a temperature of about 12–10° C. 100 g of the reaction product according to Example a (see below) which serves as the graft base, 12 g of trimethylolpropane triacrylate and 10 g of a sodium diisooctylsulphosuccinate (Rewopol V 2133 from REWO, Steinau) are now added. The initiators, a redox system consisting of 2.2 g of 2,2'-azobisamidinopropane dihydrochloride, dissolved in 20 g of water, 4.4 g of potassium peroxydisulphate, dissolved in 170 g of water, and 6 g of sodium pyrosulphite, dissolved in 120 g of water, are added in succession at a temperature of 10–12° C. and the mixture is stirred thoroughly. The reaction solution is then left to stand, without stirring, a solid gel forming as a result of the polymerization which starts, in the course of which the temperature rises up to about 85° C. This gel is then comminuted mechanically, dried at temperatures above 80° C. and ground.

The product described above was incorporated into a baby's nappy in a conventional manner and was distinguished here by a particularly good retention of liquid.

Preparation of the graft bases:

EXAMPLE a 39.2 g of maleic anhydride are introduced into 345 g of a block copolymer of 1.6 mol of propylene oxide and 0.2 mol of ethylene oxide with an OH number of 65, at room temperature and while stirring, and this mixture is heated at 80° C., with stirring. During this procedure, the maleic anhydride dissolves, the reaction being slightly exothermic, and a clear pale yellowish-coloured solution is formed.

The following reaction products were prepared in an analogous manner:

EXAMPLE b 488 g of a copolymer of 1.4 mol of propylene oxide and 0.45 mol of ethylene oxide with an OH number of 46 and 39.2 g of maleic anhydride.

EXAMPLE c 311.8 g of a copolymer of 1.05 mol of propylene oxide and 0.9 mol of ethylene oxide with an OH number of 36 and 19.6 g of maleic anhydride.

EXAMPLE d 330 g of a copolymer of 0.35 mol of propylene oxide and 1.82 mol of ethylene oxide with an OH number of 17 and 9.8 g of maleic anhydride.

EXAMPLE e 300 g of polyethylene glycol with a molecular weight of 300 and 196 g of maleic anhydride. A weak stream of nitrogen is passed in throughout the entire reaction time.

EXAMPLE f 300 g of polyethylene glycol with a molecular weight of 1,500 and 39.2 g of maleic anhydride. A weak stream of nitrogen is passed in throughout the entire reaction time.

EXAMPLE g 350 g of propylene glycol with a molecular weight of 1,750 and 39.2 g of maleic anhydride. A weak stream of nitrogen is passed in throughout the entire reaction time.

EXAMPLE 2

4,419 g of ice and 1,888 g of acrylic acid are taken in a 10 liter plastic bucket, 1,573 g of 50% strength NaOH are slowly metered in and 100 g of the reaction product according to Example 1a which serves as the graft base, 12 g of bisacrylamidoacetic acid, dispersed in 100 g of water and dissolved and brought to pH 6 by addition of NaOH, and 10 g of Rewopol V 2133 are then added.

The reaction solution is brought to 20° C., the initiators, a redox system consisting of 6 g of potassium peroxydisulphate, dissolved in 170 g of water, and 0.15 g of ascorbic acid, dissolved in 120 g of water, are then added and the mixture is left to stand, without stirring. The gel formed by polymerization is then comminuted mechanically, dried at temperatures above 80° C. and ground.

EXAMPLE 3

5,250 g of demineralized water, 1,888 g of acrylic acid and 100 g of the reaction product according to Example 1a which serves as the graft base are taken in a 10 liter polyethylene bucket. 12 g of tetraallyloxyethane and 10 g of Rewopol V 2133 are stirred in. After the reaction solution has been brought to 18–20° C., the initiators, 6 g of potassium peroxydisulphate in 170 g of water and 0.2 g of ascorbic acid in 20 g of water, are added in succession and the reaction vessel is left to stand under good insulation, without stirring. After the reaction has started, the temperature rises to about 90° C. and a solid gel forms. This is comminuted mechanically through an extruder, into which 1,555 g of 50% strength NaOH is metered continuously, partial evaporation of the water taking place. The flaky polymer is then subjected to final drying at temperatures above 80° C. and ground.

Other examples of the preparation of graft polymers according to the invention in accordance with Examples 1 and 2 described here are summarized in the following table. The quantity data denote % by weight, based on the total monomer content.

The following abbreviations are used:
AA: acrylic acid
MAA: methacrylic acid
CTA: crotonic acid
VPA vinylphosphonic acid
VPE: vinylphosphonic acid half-ester
AMPS: 2-acrylamido-2-methyl-propanesulphonic acid
AMPP: 2-acrylamido-2-methyl-propanephosphonic acid
BAAA: bisacrylamidoacetic acid
TMPTA: trimethylolpropane triacetate
TAE: tetraallyloxyethane

| Example | Prepared analogously to Example | AA (%) | MAA (%) | AMPS (%) | AMPP (%) | VPA (%) | VPE (%) | CTA (%) | Graft base according to Example | (%) | BAAA (%) | TMPTA (%) | TAE (%) | Degree of neutralisation (%) |
|---|---|---|---|---|---|---|---|---|---|---|---|---|---|---|
| 4 | 1 | 94.4 | | | | | | | 1g | 5 | | 0.6 | | 45 |
| 5 | 1 | 94.4 | | | | | | | 1d | 5 | | 0.6 | | 45 |
| 6 | 1 | 89.4 | | | | | | | 1d | 10 | | 0.6 | | 45 |
| 7 | 1 | 94.4 | | | | | | | 1e | 5 | | 0.6 | | 45 |
| 8 | 1 | 94.4 | | | | | | | 1c | 5 | | 0.6 | | 45 |
| 9 | 1 | 94.4 | | | | | | | 1b | 5 | | 0.6 | | 45 |
| 10 | 1 | 88.5 | | | | | | | 1b | 10 | | 1.5 | | 70 |
| 11 | 1 | 94.4 | | | | | | | 1f | 5 | | 0.6 | | 45 |
| 12 | 2 | 89.4 | | | | | | | 1a | 10 | 0.6 | | | 75 |
| 13 | 2 | 89.4 | | | | | | | 1a | 10 | | | 0.6 | 78 |
| 14 | 1 | 98.4 | | | | | | | 1c | 1 | | 0.6 | | 45 |
| 15 | 1 | 70.0 | 10.0 | 9.5 | | | | | 1d | 10 | | | 0.5 | 48 |
| 16 | 2 | 65.0 | | 25.0 | 4.0 | | | | 1c | 5 | 1.0 | | | 45 |
| 17 | 2 | 75.0 | 5.0 | 10.0 | | | 4.2 | | 1c | 5 | | 0.8 | | 60 |
| 18 | 2 | 85.0 | | 5.0 | 4.5 | | | | 1c | 5 | 0.5 | | | 70 |
| 19 | 1 | 72.0 | | 20.0 | | 4.2 | | | 1b | 3 | 0.8 | | | 80 |
| 20 | 1 | 81.0 | 10.0 | | | 4.0 | | | 1c | 4 | | 1.0 | | 36 |
| 21 | 2 | 90.0 | | | 4.6 | | | | 1c | 5 | | | 0.4 | 25 |
| 22 | 2 | 79.0 | | 19.0 | | | | | 1f | 1 | | | 1.0 | 40 |
| 23 | 1 | 72.0 | | 19.3 | | | 5.0 | | 1c | 3 | | | 0.7 | 48 |
| 24 | 1 | 90.0 | | | | 1.0 | | | 1c | 8 | | | 1.0 | 32 |

What is claimed is:

1. Hydrophilic swellable graft polymers which consists, in random distribution, to the extent of 0.5 to 20% by weight of said graft polymer, radicals of the general formula I

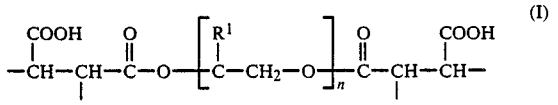 (I)

having grafted thereon, to the extent of 79 to 99% by weight of said graft polymer, radicals containing an acid group, of the general formula II

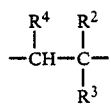 (II)

and to the extent of 0.1 to 2% by eight of crosslinking structures originating from monomers with at least two olefinically unsaturated double bonds, wherein n denotes 2 to 300, R¹ denotes hydrogen or methyl, R² denotes hydrogen, methyl or ethyl, R³ denotes the carboxyl group, the group -SO₃H, the group -PO₃R⁸R⁹, wherein R⁸ and R⁹ denote independently from one another hydrogen or alkyl with 1 to 4 carbon atoms or a group of the formula

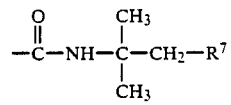

wherein R⁷ stands for the group -SO₃H or the group -PO₃H₂, and

R⁴ denotes hydrogen, methyl, ethyl or the carboxyl group.

2. Graft polymers according to claim 1, characterized in that they consists, in random distribution, to the extent of 1 to 10.5% by weight of radicals of the general formula I, to the extent of 88 to 98.5% by weight of radicals of the general formula II and to the extent of 0.3 to 1.5% by weight of crosslinking structures.

3. Graft polymers according to claim 1, characterized in that the radicals of the general formula 1 differ from one another in respect of the radical R¹ or the number n or both.

4. Graft polymers according to claim 1, characterized in that the radicals of the general formula II, R² denotes hydrogen or methyl, R³ denotes the carboxyl group, the group -SO₃H or the group -PO₃R⁸R⁹ and R⁴ denotes hydrogen.

5. Graft polymers according to claim 1, characterized in that in the radicals of the general formula II, R³ denotes the carboxyl group.

6. Graft polymers according to claim 1, characterized in that the crosslinking structures are derived from monomers with at least two alkenyl groups or at least two alkenoyl groups, in particular from bisacrylamidoacetic acid, trimethylolpropane triacrylate or tetraallyloxyethane.

* * * * *